US008460695B2

(12) United States Patent
Greenawalt

(10) Patent No.: US 8,460,695 B2
(45) Date of Patent: Jun. 11, 2013

(54) MAKING A SOFT TISSUE PROSTHESIS FOR REPAIRING A DEFECT OF AN ABDOMINAL WALL OR A PELVIC CAVITY WALL

(71) Applicant: Genzyme Corporation, Cambridge, MA (US)

(72) Inventor: Keith E. Greenawalt, Milton, MA (US)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 13/658,385

(22) Filed: Oct. 23, 2012

(65) Prior Publication Data

US 2013/0045327 A1 Feb. 21, 2013

Related U.S. Application Data

(62) Division of application No. 11/103,967, filed on Apr. 12, 2005, now Pat. No. 8,323,675.

(60) Provisional application No. 60/563,836, filed on Apr. 20, 2004.

(51) Int. Cl.
*A61F 2/00* (2006.01)

(52) U.S. Cl.
USPC .......................................... 424/423; 424/426

(58) Field of Classification Search
None
See application file for complete search history.

(56) References Cited

U.S. PATENT DOCUMENTS

| 4,006,747 | A | 2/1977 | Kronenthal et al. |
| 4,014,434 | A | 3/1977 | Thyen |
| 4,034,850 | A | 7/1977 | Mandel et al. |
| 4,052,988 | A | 10/1977 | Doddi et al. |
| 4,069,151 | A | 1/1978 | Higley et al. |
| 4,137,921 | A | 2/1979 | Okuzumi et al. |
| 4,140,678 | A | 2/1979 | Shalaby et al. |
| 4,141,087 | A | 2/1979 | Shalaby et al. |
| 4,194,041 | A | 3/1980 | Gore et al. |
| 4,199,649 | A | 4/1980 | Yundt |
| 4,205,399 | A | 6/1980 | Shalaby et al. |
| 4,206,024 | A | 6/1980 | Carpenter et al. |
| 4,365,634 | A | 12/1982 | Bare et al. |
| 4,388,926 | A | 6/1983 | Shalaby et al. |
| 4,393,584 | A | 7/1983 | Bare et al. |
| 4,441,496 | A | 4/1984 | Shalaby et al. |
| 4,491,218 | A | 1/1985 | Aday |
| 4,511,035 | A | 4/1985 | Alpern |
| 4,511,706 | A | 4/1985 | Shalaby et al. |
| 4,519,501 | A | 5/1985 | Cerwin |

(Continued)

FOREIGN PATENT DOCUMENTS

| CA | 2365543 | 6/2002 |
| EP | 1099421 | 5/2001 |

(Continued)

OTHER PUBLICATIONS

Wantz, "Incisional Hernioplasty with Mersilene," Surgery, Gynecology & Obstetrics, vol. 172 (Feb. 1991).

(Continued)

*Primary Examiner* — Carlos Azpuru
*Assistant Examiner* — Casey Hagopian
(74) *Attorney, Agent, or Firm* — Fish & Richardson P.C.

(57) ABSTRACT

Surgical prostheses and methods of using and making surgical prostheses are disclosed.

19 Claims, 11 Drawing Sheets

U.S. PATENT DOCUMENTS

| | | | |
|---|---|---|---|
| 4,520,821 A | 6/1985 | Schmidt et al. |
| 4,522,211 A | 6/1985 | Bare et al. |
| 4,533,041 A | 8/1985 | Aday et al. |
| 4,543,952 A | 10/1985 | Shalaby et al. |
| 4,550,730 A | 11/1985 | Shalaby et al. |
| 4,561,858 A | 12/1985 | Allen, Jr. et al. |
| 4,578,063 A | 3/1986 | Inman et al. |
| 4,604,097 A | 8/1986 | Graves, Jr. et al. |
| 4,608,428 A | 8/1986 | Shalaby et al. |
| 4,612,230 A | 9/1986 | Liland et al. |
| 4,615,435 A | 10/1986 | Alpern et al. |
| 4,642,111 A | 2/1987 | Sakamoto et al. |
| 4,650,817 A | 3/1987 | Allen, Jr. et al. |
| 4,652,264 A | 3/1987 | Dumican |
| 4,659,572 A | 4/1987 | Murray |
| 4,670,286 A | 6/1987 | Nyilas et al. |
| 4,680,220 A | 7/1987 | Johnson |
| 4,692,369 A | 9/1987 | Nomi |
| 4,747,897 A | 5/1988 | Johnson |
| 4,767,619 A | 8/1988 | Murray |
| 4,769,038 A | 9/1988 | Bendavid et al. |
| 4,772,509 A | 9/1988 | Komada et al. |
| 4,796,603 A | 1/1989 | Dahlke et al. |
| 4,823,805 A | 4/1989 | Wojcik |
| 4,871,365 A | 10/1989 | Dumican |
| 4,895,566 A | 1/1990 | Lee |
| 4,905,694 A | 3/1990 | Will |
| 4,925,732 A | 5/1990 | Driskill et al. |
| 4,937,270 A | 6/1990 | Hamilton et al. |
| 4,946,736 A | 8/1990 | Sassa |
| 4,990,158 A | 2/1991 | Kaplan et al. |
| 4,997,440 A | 3/1991 | Dumican |
| 4,999,235 A | 3/1991 | Lunn et al. |
| 5,017,229 A * | 5/1991 | Burns et al. ................ 106/162.2 |
| 5,026,591 A | 6/1991 | Henn et al. |
| 5,026,607 A | 6/1991 | Kiezulas |
| 5,034,801 A | 7/1991 | Fischer |
| 5,077,352 A | 12/1991 | Elton |
| 5,092,884 A | 3/1992 | Devereux et al. |
| 5,108,474 A | 4/1992 | Riedy et al. |
| 5,130,024 A | 7/1992 | Fujimoto et al. |
| 5,141,522 A | 8/1992 | Landi |
| 5,147,332 A | 9/1992 | Moorehead |
| 5,160,790 A | 11/1992 | Elton |
| 5,179,174 A | 1/1993 | Elton |
| 5,188,890 A | 2/1993 | Ohashi et al. |
| 5,207,812 A | 5/1993 | Tronto et al. |
| 5,209,969 A | 5/1993 | Crowther |
| 5,217,797 A | 6/1993 | Knox et al. |
| 5,234,106 A | 8/1993 | Transue et al. |
| 5,256,764 A | 10/1993 | Tang et al. |
| 5,258,010 A | 11/1993 | Green et al. |
| 5,263,629 A | 11/1993 | Trumbull et al. |
| 5,264,540 A | 11/1993 | Cooper et al. |
| 5,269,810 A | 12/1993 | Hull et al. |
| 5,272,012 A | 12/1993 | Opolski |
| 5,274,074 A | 12/1993 | Tang et al. |
| 5,279,539 A | 1/1994 | Bohan et al. |
| 5,281,475 A | 1/1994 | Hollenbaugh, Jr. et al. |
| 5,284,138 A | 2/1994 | Kujawski |
| 5,284,240 A | 2/1994 | Alpern et al. |
| 5,284,244 A | 2/1994 | O'Toole et al. |
| 5,288,552 A | 2/1994 | Hollenbaugh, Jr. et al. |
| 5,290,585 A | 3/1994 | Elton |
| 5,292,328 A | 3/1994 | Hain et al. |
| 5,292,333 A | 3/1994 | Johnson |
| 5,311,884 A | 5/1994 | Scopelianos |
| 5,320,624 A | 6/1994 | Kaplan et al. |
| 5,321,113 A | 6/1994 | Cooper et al. |
| 5,325,987 A | 7/1994 | Alpern et al. |
| 5,326,355 A | 7/1994 | Landi |
| 5,330,489 A | 7/1994 | Green et al. |
| 5,339,833 A | 8/1994 | Berthiaume et al. |
| 5,352,511 A | 10/1994 | Abayasekara et al. |
| 5,354,587 A | 10/1994 | Abayasekara |
| 5,356,006 A | 10/1994 | Alpern et al. |
| 5,356,432 A | 10/1994 | Rutkow et al. |
| 5,356,883 A | 10/1994 | Kuo et al. |
| 5,358,475 A | 10/1994 | Mares et al. |
| 5,364,699 A | 11/1994 | Hollenbaugh, Jr. et al. |
| 5,366,504 A | 11/1994 | Andersen et al. |
| 5,379,472 A | 1/1995 | Aihomaki |
| 5,383,925 A | 1/1995 | Schmitt |
| 5,392,978 A | 2/1995 | Velez et al. |
| 5,393,594 A | 2/1995 | Koyfman et al. |
| 5,395,383 A | 3/1995 | Adams et al. |
| 5,397,332 A | 3/1995 | Kammerer et al. |
| 5,410,016 A | 4/1995 | Hubbell et al. |
| 5,412,068 A | 5/1995 | Tang et al. |
| 5,413,598 A | 5/1995 | Moreland |
| 5,424,136 A | 6/1995 | Hermes |
| 5,429,869 A | 7/1995 | McGregor et al. |
| 5,433,996 A | 7/1995 | Kranzler et al. |
| 5,437,900 A | 8/1995 | Kuzowski |
| 5,445,739 A | 8/1995 | Fujimoto et al. |
| 5,454,820 A | 10/1995 | Kammerer et al. |
| 5,462,781 A | 10/1995 | Zukowski |
| 5,464,929 A | 11/1995 | Bezwada et al. |
| 5,478,372 A | 12/1995 | Stark |
| 5,478,423 A | 12/1995 | Sassa et al. |
| 5,486,593 A | 1/1996 | Tang et al. |
| 5,494,620 A | 2/1996 | Liu et al. |
| 5,498,467 A | 3/1996 | Meola |
| 5,500,038 A | 3/1996 | Dauber et al. |
| 5,516,881 A | 5/1996 | Lee et al. |
| 5,522,879 A | 6/1996 | Scopelianos |
| 5,527,893 A * | 6/1996 | Burns et al. ................ 514/53 |
| 5,529,830 A | 6/1996 | Dutta et al. |
| 5,531,998 A | 7/1996 | Mares et al. |
| 5,541,076 A | 7/1996 | Houghton et al. |
| 5,542,594 A | 8/1996 | McKean et al. |
| 5,547,551 A | 8/1996 | Bahar et al. |
| 5,565,154 A | 10/1996 | McGregor et al. |
| 5,567,435 A | 10/1996 | Hubbell et al. |
| 5,569,273 A | 10/1996 | Titone et al. |
| 5,571,126 A | 11/1996 | Dorsey, III |
| 5,571,605 A | 11/1996 | Abrams et al. |
| 5,584,875 A | 12/1996 | Duhamel et al. |
| 5,591,526 A | 1/1997 | Abrams et al. |
| 5,593,441 A | 1/1997 | Lichtenstein et al. |
| 5,595,751 A | 1/1997 | Bezwada et al. |
| 5,597,579 A | 1/1997 | Bezwada et al. |
| 5,599,614 A | 2/1997 | Bahar et al. |
| 5,607,687 A | 3/1997 | Bezwada et al. |
| 5,614,284 A | 3/1997 | Kranzler et al. |
| 5,618,552 A | 4/1997 | Bezwada et al. |
| 5,620,669 A | 4/1997 | Plinke et al. |
| 5,620,698 A | 4/1997 | Bezwada et al. |
| 5,626,611 A | 5/1997 | Liu et al. |
| 5,626,811 A | 5/1997 | Liu |
| 5,631,011 A | 5/1997 | Wadstrom |
| 5,632,745 A | 5/1997 | Schwartz |
| 5,632,979 A | 5/1997 | Goldberg et al. |
| 5,633,343 A | 5/1997 | Bezwada et al. |
| 5,635,041 A | 6/1997 | Bahar et al. |
| 5,635,124 A | 6/1997 | Abrams et al. |
| 5,639,851 A | 6/1997 | Bezwada et al. |
| 5,641,501 A | 6/1997 | Cooper et al. |
| 5,644,002 A | 7/1997 | Cooper et al. |
| 5,645,850 A | 7/1997 | Bezwada et al. |
| 5,648,088 A | 7/1997 | Bezwada et al. |
| 5,652,055 A | 7/1997 | King et al. |
| 5,658,894 A | 8/1997 | Weisz |
| 5,660,918 A | 8/1997 | Dutta |
| 5,688,900 A | 11/1997 | Cooper et al. |
| 5,690,739 A | 11/1997 | Sassa et al. |
| 5,695,525 A | 12/1997 | Mulhauser et al. |
| 5,696,178 A | 12/1997 | Cooper et al. |
| 5,698,213 A | 12/1997 | Jamiolkowski et al. |
| 5,700,583 A | 12/1997 | Jamiolkowski et al. |
| 5,703,200 A | 12/1997 | Bezwada et al. |
| 5,705,177 A | 1/1998 | Roufa et al. |
| 5,705,181 A | 1/1998 | Cooper et al. |
| 5,709,748 A | 1/1998 | Sassa et al. |
| 5,709,954 A | 1/1998 | Lyden et al. |
| 5,714,389 A | 2/1998 | Charlton et al. |
| 5,714,551 A | 2/1998 | Bezwada et al. |

| | | | | | | |
|---|---|---|---|---|---|---|
| 5,716,408 A | 2/1998 | Eldridge et al. | | 6,120,539 A | 9/2000 | Eldridge et al. |
| 5,733,325 A | 3/1998 | Robinson et al. | | 6,130,175 A | 10/2000 | Rusch et al. |
| 5,736,589 A | 4/1998 | Cooper et al. | | 6,138,278 A | 10/2000 | Taylor et al. |
| 5,749,968 A | 5/1998 | Melanson et al. | | 6,143,675 A | 11/2000 | McCollam et al. |
| 5,759,154 A | 6/1998 | Hoyns | | 6,147,168 A | 11/2000 | Jamiolkowski et al. |
| 5,766,246 A | 6/1998 | Mulhauser et al. | | 6,150,581 A | 11/2000 | Jiang et al. |
| 5,766,979 A | 6/1998 | Budnaitis | | 6,152,141 A | 11/2000 | Stevens et al. |
| 5,769,862 A | 6/1998 | Kammerer et al. | | 6,162,962 A | 12/2000 | Hinsch et al. |
| 5,769,899 A | 6/1998 | Schwartz et al. | | 6,165,217 A | 12/2000 | Hayes |
| 5,776,611 A | 7/1998 | Elton et al. | | 6,171,330 B1 | 1/2001 | Benchetrit |
| 5,786,057 A | 7/1998 | Lyden et al. | | 6,177,095 B1 * | 1/2001 | Sawhney et al. .............. 424/426 |
| 5,788,770 A | 8/1998 | Hobson et al. | | 6,214,020 B1 | 4/2001 | Mulhauser et al. |
| 5,795,584 A | 8/1998 | Totakura et al. | | 6,214,039 B1 | 4/2001 | Banas et al. |
| 5,800,908 A | 9/1998 | Hobson et al. | | 6,214,331 B1 | 4/2001 | Vanderhoff et al. |
| 5,804,011 A | 9/1998 | Dutta et al. | | 6,216,496 B1 | 4/2001 | Gehring |
| 5,815,125 A | 9/1998 | Kelly et al. | | 6,221,099 B1 | 4/2001 | Andersen et al. |
| 5,820,552 A | 10/1998 | Crosby et al. | | 6,224,622 B1 | 5/2001 | Kotzev |
| 5,820,841 A | 10/1998 | Chen et al. | | 6,224,828 B1 | 5/2001 | Lin et al. |
| 5,824,047 A | 10/1998 | Moreland | | 6,224,894 B1 | 5/2001 | Jamiolkowski et al. |
| 5,830,565 A | 11/1998 | Budnaitis | | 6,233,905 B1 | 5/2001 | Singh |
| 5,837,001 A | 11/1998 | Mackey | | 6,235,659 B1 | 5/2001 | McAmish et al. |
| 5,843,268 A | 12/1998 | Lyden et al. | | 6,238,467 B1 | 5/2001 | Azarian et al. |
| 5,843,390 A | 12/1998 | Plinke et al. | | 6,241,763 B1 | 6/2001 | Drasler et al. |
| 5,843,743 A | 12/1998 | Hubbell et al. | | 6,245,030 B1 | 6/2001 | DuBois et al. |
| 5,844,016 A | 12/1998 | Sawhney et al. | | 6,245,098 B1 | 6/2001 | Feeser et al. |
| 5,844,017 A | 12/1998 | Jamiolkowski et al. | | 6,251,135 B1 | 6/2001 | Stinson et al. |
| 5,847,327 A | 12/1998 | Fischer et al. | | 6,251,435 B1 | 6/2001 | Jamiolkowski et al. |
| 5,854,383 A | 12/1998 | Erneta et al. | | 6,253,769 B1 | 7/2001 | LaFontaine et al. |
| 5,859,150 A | 1/1999 | Jamiolkowski et al. | | 6,254,978 B1 | 7/2001 | Bahar et al. |
| 5,868,788 A | 2/1999 | Bezwada et al. | | 6,258,017 B1 | 7/2001 | Singh |
| 5,874,419 A | 2/1999 | Herrmann et al. | | 6,258,124 B1 | 7/2001 | Darois et al. |
| 5,874,537 A | 2/1999 | Kelman et al. | | 6,264,684 B1 | 7/2001 | Banas et al. |
| 5,885,738 A | 3/1999 | Hannon | | 6,264,702 B1 | 7/2001 | Ory et al. |
| 5,886,535 A | 3/1999 | Budnaitis | | 6,267,772 B1 | 7/2001 | Mulhauser et al. |
| 5,891,193 A | 4/1999 | Robinson et al. | | RE37,307 E | 8/2001 | Bahar et al. |
| 5,896,038 A | 4/1999 | Budnaitis et al. | | 6,270,530 B1 | 8/2001 | Eldridge et al. |
| 5,902,799 A | 5/1999 | Herrmann et al. | | 6,270,902 B1 | 8/2001 | Tedeschi et al. |
| 5,902,956 A | 5/1999 | Spies et al. | | 6,283,905 B1 | 9/2001 | Singh |
| 5,906,872 A | 5/1999 | Lyden et al. | | 6,287,316 B1 | 9/2001 | Agarwal et al. |
| 5,908,427 A | 6/1999 | McKean et al. | | 6,287,499 B1 | 9/2001 | Roby et al. |
| 5,908,428 A | 6/1999 | Scirica et al. | | 6,294,202 B1 | 9/2001 | Burns et al. |
| 5,909,123 A | 6/1999 | Budnaitis | | 6,294,356 B1 | 9/2001 | Jones et al. |
| 5,916,671 A | 6/1999 | Dauber et al. | | 6,296,691 B1 | 10/2001 | Gidumal |
| 5,928,414 A | 7/1999 | Wnenchak et al. | | 6,306,164 B1 | 10/2001 | Kujawski |
| 5,931,835 A | 8/1999 | Mackey | | 6,306,424 B1 | 10/2001 | Vyakarnam et al. |
| 5,935,161 A | 8/1999 | Robinson et al. | | 6,309,423 B2 | 10/2001 | Hayes |
| 5,935,940 A | 8/1999 | Weisz | | 6,313,411 B1 | 11/2001 | Budnaitis |
| 5,951,997 A | 9/1999 | Bezwada et al. | | 6,319,264 B1 | 11/2001 | Tormala et al. |
| 5,962,023 A | 10/1999 | Jamiolkowski et al. | | 6,324,435 B1 | 11/2001 | Shchervinsky et al. |
| 5,964,774 A | 10/1999 | McKean et al. | | 6,329,488 B1 | 12/2001 | Terry et al. |
| 5,966,022 A | 10/1999 | Budnaitis et al. | | 6,331,351 B1 | 12/2001 | Waters et al. |
| 5,966,593 A | 10/1999 | Budnaitis et al. | | 6,332,884 B1 | 12/2001 | Cooper |
| 5,976,127 A | 11/1999 | Lax | | 6,333,029 B1 | 12/2001 | Vyakarnam et al. |
| 5,986,043 A | 11/1999 | Hubbell et al. | | 6,344,371 B2 | 2/2002 | Fischer et al. |
| 5,997,568 A | 12/1999 | Liu | | 6,350,244 B1 | 2/2002 | Fisher |
| 6,004,326 A | 12/1999 | Castro et al. | | 6,350,283 B1 | 2/2002 | Michelson |
| 6,004,347 A | 12/1999 | McNamara et al. | | 6,352,710 B2 | 3/2002 | Sawhney et al. |
| 6,026,814 A | 2/2000 | LaFontaine et al. | | 6,355,699 B1 | 3/2002 | Vakarnam et al. |
| 6,029,806 A | 2/2000 | Cerwin et al. | | 6,361,551 B1 | 3/2002 | Torgerson et al. |
| 6,031,148 A | 2/2000 | Hayes et al. | | RE37,656 E | 4/2002 | Bahar et al. |
| 6,039,755 A | 3/2000 | Edwin et al. | | 6,372,256 B2 | 4/2002 | Jamiolkowski et al. |
| 6,041,211 A | 3/2000 | Hobson et al. | | RE37,701 E | 5/2002 | Bahar et al. |
| 6,045,560 A | 4/2000 | McKean et al. | | 6,385,946 B1 | 5/2002 | Singh |
| 6,045,571 A | 4/2000 | Hill et al. | | 6,387,363 B1 | 5/2002 | Gruskin |
| 6,046,060 A | 4/2000 | Budnaitis | | 6,391,060 B1 | 5/2002 | Ory et al. |
| 6,054,230 A | 4/2000 | Kato | | 6,395,017 B1 | 5/2002 | Dwyer et al. |
| 6,063,112 A | 5/2000 | Sgro | | 6,403,655 B1 | 6/2002 | Bezwada et al. |
| 6,063,115 A | 5/2000 | Gealow | | 6,406,423 B1 | 6/2002 | Seetbon |
| 6,066,294 A | 5/2000 | Lin et al. | | 6,408,656 B1 | 6/2002 | Ory et al. |
| 6,066,777 A | 5/2000 | Benchetrit | | 6,410,044 B1 | 6/2002 | Chudzik et al. |
| 6,074,660 A | 6/2000 | Jamiolkowski et al. | | 6,423,252 B1 | 7/2002 | Chun et al. |
| 6,077,297 A | 6/2000 | Robinson et al. | | 6,425,547 B1 | 7/2002 | Singh |
| 6,083,524 A | 7/2000 | Sawhney et al. | | 6,425,924 B1 | 7/2002 | Rousseau |
| 6,086,526 A | 7/2000 | Franschelli | | 6,440,427 B1 | 8/2002 | Wadstrom |
| 6,100,346 A | 8/2000 | Jamiolkowski et al. | | 6,443,964 B1 | 9/2002 | Ory et al. |
| 6,110,243 A | 8/2000 | Wnenchak et al. | | 6,447,551 B1 | 9/2002 | Goldmann |
| 6,113,624 A | 9/2000 | Bezwada et al. | | 6,451,032 B1 | 9/2002 | Ory et al. |
| 6,117,095 A | 9/2000 | Daggett et al. | | 6,451,059 B1 | 9/2002 | Janas et al. |
| 6,117,528 A | 9/2000 | Hobson et al. | | 6,458,385 B2 | 10/2002 | Jamiolkowski et al. |

| | | |
|---|---|---|
| 6,458,554 B1 | 10/2002 | Hui et al. |
| 6,461,311 B2 | 10/2002 | DuBois et al. |
| 6,478,727 B2 | 11/2002 | Seetbon |
| 6,482,444 B1 | 11/2002 | Bellantone et al. |
| 6,497,650 B1 * | 12/2002 | Nicolo ............................ 600/37 |
| 6,500,777 B1 | 12/2002 | Wiseman et al. |
| 6,503,257 B2 | 1/2003 | Grant et al. |
| 6,506,197 B1 | 1/2003 | Rollero et al. |
| 6,524,345 B1 | 2/2003 | Valimaa et al. |
| 6,528,015 B1 | 3/2003 | Lin et al. |
| 6,531,147 B2 | 3/2003 | Sawhney et al. |
| 6,534,084 B1 | 3/2003 | Vyakarnam et al. |
| 6,544,503 B1 | 4/2003 | Vanderhoff et al. |
| 6,546,603 B1 | 4/2003 | Wang et al. |
| 6,547,801 B1 | 4/2003 | Dargent et al. |
| 6,548,081 B2 | 4/2003 | Sadozai et al. |
| 6,551,555 B2 | 4/2003 | Antonoplos et al. |
| 6,562,068 B2 | 5/2003 | Drasler et al. |
| 6,565,580 B1 | 5/2003 | Beretta |
| 6,565,842 B1 | 5/2003 | Sojomihardjo et al. |
| 6,575,168 B2 | 6/2003 | LaFontaine et al. |
| 6,592,515 B2 | 7/2003 | Thierfelder et al. |
| 6,592,625 B2 | 7/2003 | Cauthen |
| 6,602,290 B2 | 8/2003 | Esnouf et al. |
| 6,638,284 B1 | 10/2003 | Rousseau et al. |
| 6,737,371 B1 | 5/2004 | Planck et al. |
| 2002/0018813 A1 | 2/2002 | Burns et al. |
| 2003/0078602 A1 | 4/2003 | Rousseau |
| 2003/0100955 A1 | 5/2003 | Greenawalt |
| 2003/0225355 A1 | 12/2003 | Butler |
| 2005/0181023 A1 | 8/2005 | Young et al. |

FOREIGN PATENT DOCUMENTS

| | | |
|---|---|---|
| JP | 4250167 | 9/1992 |
| WO | WO94/06373 | 3/1994 |
| WO | WO98/12243 | 3/1998 |
| WO | WO00/16822 | 3/2000 |
| WO | WO01/43789 | 6/2001 |
| WO | WO03/041613 | 5/2003 |
| WO | WO03/084410 | 10/2003 |

OTHER PUBLICATIONS

Greenawalt et al, "Evaluation of Sepramesh Biosurgical Composite in a Rabbit Hernia Repair Model," Journal of Surgical Research, Academic Press, Inc, San Diego, CA, vol. 94, pp. 92-98 (Dec. 2000).

Notice of Reasons of Rejection of JP 2007-509511 mailed May 10, 2011.

Office Action from corresponding Canadian Patent Appn. No. 2563347 dated Nov. 18, 2011.

Office Action from corresponding European Patent Appn. No. 05732926.0 dated Nov. 15, 2012.

* cited by examiner

MAKING A SOFT TISSUE PROSTHESIS FOR REPAIRING A DEFECT OF AN ABDOMINAL WALL OR A PELVIC CAVITY WALL

CROSS-REFERENCE TO RELATED APPLICATIONS

This application is a divisional application of and claims priority to U.S. application Ser. No. 11/103,967, filed on Apr. 12, 2005, which application claims priority to U.S. Application Ser. No. 60/563,836, filed on Apr. 20, 2004, the entire contents of both are incorporated by reference herein.

TECHNICAL FIELD

This invention relates to surgical prostheses, and more particularly to a surgical prosthesis used to repair an opening in a body cavity.

BACKGROUND

An unwanted opening in a body cavity, such as an incisional hernia, is often repaired using a prosthetic mesh, such as a polypropylene mesh or a polypropylene mesh including a biodegradable, adhesion barrier layer as described in PCT publication number WO 01/43789 and U.S. Pat. No. 6,264,702, to line the inner surface of the body cavity at the wall opening.

SUMMARY

In general, in one aspect, the invention features a surgical prosthesis. The surgical prosthesis includes a three-dimensional mesh including at least two types of yarn interlooped or intertwined to define at least two layers, wherein one of the at least two layers is substantially non-biodegradable and another of the at least two layers is substantially biodegradable. An adhesion barrier is interconnected with the second, substantially biodegradable layer of the three-dimensional mesh.

Embodiments may include one or more of the following features. One of the at least two types of yarn within the three-dimensional mesh is a non-biodegradable yarn. The non-biodegradable yarn is selected from polypropylene, polyethylene terephthalate or a combination thereof. The non-biodegradable yarn has a diameter of about 0.001 to about 0.010 inches, and is preferably about 0.005 inches.

Embodiments may also include one or more of the following features. One of the at least two types of yarn is a biodegradable yarn. The biodegradable yarn is selected from poly(glycolic) acid, polylactic acid, polydioxanone, polycaprolactone, calcium alginate or a combination thereof. The biodegradable yarn has a diameter of no greater than about 120 denier. In certain embodiments, the biodegradable yarn has a diameter no greater than about 100 denier.

In some embodiments, the three-dimensional mesh of the surgical prosthesis includes at least one non-biodegradable monofilament yarn and at least one biodegradable multifilament yarn. In some embodiments, the three-dimensional mesh of the surgical prosthesis includes at least one non-biodegradable monofilament yarn and at least two biodegradable multifilament yarns.

Embodiments may also include one or more of the following features. The adhesion barrier of the surgical prosthesis includes polymer hydrogel. The adhesion barrier includes at least one polyanionic polysaccharide modified by reaction with carbodiimide. In some embodiments, the adhesion barrier includes a crosslinked polymer hydrogel alone or in combination with at least one polyanionic polysaccharide modified by reaction with carbodiimide. The crosslinked polymer hydrogel includes one or more hydrophilic blocks, one or more biodegradable blocks, and one or more crosslinking blocks. The crosslinked polymer hydrogel is formed by polymerization of monomers including photopolymerizable poly(ethylene glycol)-trimethlyene carbonate/lactate multi-block polymers endcapped with acrylate esters. The polyanionic polysaccharide modified by reaction with carbodiimide includes carbodiimide-modified hyaluronic acid and carbodiimide-modified carboxymethylcellulose.

Embodiments may also include one or more of the following features. The adhesion barrier is in the form of a film, a foam, or a gel. The adhesion barrier has a density of about 5 grams total polymer per square foot. The surgical prosthesis has a moisture content of less than about 2%. In some embodiments, the surgical prosthesis has a moisture content less than about 1.2%.

In another aspect, the invention features a surgical prosthesis including a first layer formed substantially of a non-biodegradable yarn, a second layer formed substantially of a first biodegradable yarn, and an adhesion barrier embedded within the second layer. The first and second layers of the surgical prosthesis are connected with a second biodegradable yarn. The first layer defines a first outer surface of the surgical prosthesis and the adhesion barrier defines a second outer surface of the surgical prosthesis, wherein the first outer surface has a macroporous structure adapted to permit tissue ingrowth into the first layer and the second outer surface of the surgical prosthesis is adapted to minimize the formation of adhesion of tissue adjacent to the second outer surface.

Embodiments may include one or more of the following features. The second outer surface of the surgical prosthesis has a microporous structure having a pore size of about 10 microns or less. The macroporous structure of the first outer surface of the surgical prosthesis has a pore size of about 100 microns or more.

Embodiments may also include one or more of the following features. The non-biodegradable yarn is selected from polypropylene, polyethylene terephthalate or a combination thereof. The first biodegradable yarn is selected from poly(glycolic) acid, polylactic acid, polydioxanone, polycaprolactone, calcium alginate or combinations thereof. The second biodegradable yarn is selected from poly(glycolic) acid, polylactic acid, polydioxanone, polycaprolactone, calcium alginate or combinations thereof.

Embodiments may also include one or more of the following. The adhesion barrier includes a crosslinked polymer hydrogel and at least one polyanionic polysaccharide modified by reaction with carbodiimide. The crosslinked polymer hydrogel includes one or more hydrophilic blocks, one or more biodegradable blocks, and one or more crosslinking blocks. In some embodiments, the crosslinked polymer hydrogel is formed by polymerization of monomers including photopolymerizable poly(ethylene glycol)-trimethlyene carbonate/lactate multi-block polymers endcapped with acrylate esters. The polyanionic polysaccharide modified by reaction with carbodiimide includes carbodiimide-modified hyaluronic acid and carbodiimide-modified carboxymethylcellulose.

In general, in a further aspect, the invention features a method of making a surgical prosthesis. The method includes the steps of providing a fabric including a first layer formed substantially of non-biodegradable yarn and a second layer formed of biodegradable yarn, providing a liquid formulation including macromers and an initiator, placing the fabric with the liquid formulation such that the second layer is in fluid contact with the liquid formulation; and exposing the liquid formulation to a light source.

Embodiments may include one or more of the following. The light source used is an LED array having an intensity of about 1 to about 100 mW/cm². The initiator used within the liquid formulation is a photoinitiator, such as for example, Eosin Y. The liquid formulation further includes biopolymers, an accelerant, and a buffer. The biopolymers include at least one polyanionic polysaccharide modified by reaction with carbodiimide. The buffer includes triethanolamine and/or potassium phosphate. The accelerant includes N-vinylcaprolactam. In some embodiments, the liquid formulation includes 1 weight percent carbodiimide-modified hyaluronic acid and carbodiimide-modified carboxymethylcellulose, 2.5 weight percent poly(ethylene glycol)-trimethlyene carbonate/lactate multi-block polymers endcapped with acrylate esters, 40 ppm of Eosin Y, 4000 ppm N-vinylcaprolactam, 0.54 weight percent triethanolamine, 0.8 weight percent of potassium phosphate.

In another aspect, the invention features a method of making a surgical prosthesis. The method includes providing a fabric including a first layer formed substantially of non-biodegradable yarn and a second layer formed of biodegradable yarn, providing a liquid formulation including a first polymer system, a second polymer system, and a photo initiator, placing the fabric over the liquid formulation such that the second layer is in fluid contact with the liquid formulation, and exposing the liquid formulation to a light source to activate the photoinitiator so as to cause polymerization of at least one of the polymer systems in the liquid formulation.

Embodiments may include one or more of the following. The polymerization of at least one of the polymer systems results in the formation of a barrier layer partially embedded within the second layer of the fabric. The first polymer system includes carbodiimide-modified hyaluronic acid and carbodiimide-modified carboxymethylcellulose and the second polymer system includes poly(ethylene glycol)-trimethylene carbonate/lactate multi-block polymers endcapped with acrylate esters. The photoinitiator includes Eosin Y. The liquid formulation further includes an accelerant and at least one buffer. In some embodiments, the liquid formulation includes accelerant, such as, for example, n-vinylcaprolactam, and two buffers, such as triethanolamine and potassium phosphate.

Embodiments may also include one or more of the following. The light source used to activate the photoinitiator is an LED array having an intensity of about 1 to about 100 mW/cm². The surgical prosthesis formed is dried in a convection oven.

In general, in a further aspect, the invention features a method of repairing an opening in a wall enclosing a body cavity of a patient. The method includes providing a surgical prosthesis, such as, for example, the surgical prostheses described above, and securing the surgical prosthesis over the wall opening of the patient such that the adhesion barrier faces viscera or tissue from which adhesion is to be prevented.

Embodiments may have one or more of the following advantages. The surgical prosthesis can be used to treat an opening in a patient's body cavity with minimal or no adhesion formation. Due to the incorporation of the adhesion barrier within the mesh, there is a strong mechanical connection between the hydrophilic adhesion barrier and a hydrophobic polypropylene mesh. As a result, the likelihood of delamination of the adhesion barrier from the mesh is decreased. Another advantage of the surgical prosthesis is the inclusion of interlooping or intertwining yarns forming the two layers of the mesh. The use of the interlooping or intertwining yarns reduces or even eliminates reliance on adhesives to form the surgical prosthesis.

As used herein "non-biodegradable" means a material that contains components that are not readily degraded, absorbed, or otherwise decomposed when present in a body cavity.

As used herein "biodegradable" means a material that contains components that can be degraded and/or absorbed at some time after implantation of the surgical prosthesis, such as within weeks or months following implantation.

As used herein "substantially" means predominantly but not wholly that which is specified. When a layer is said to be substantially non-biodegradable, it refers to a layer that is predominantly composed of non-biodegradable material, but for a small volume of the layer where the non-biodegradable material intertwines with the biodegradable material. When a layer is said to be substantially biodegradable, it refers to a layer that is predominantly composed of biodegradable material, but for a small volume of the layer where the biodegradable material intertwines with the non-biodegradable material.

The details of one or more embodiments of the invention are set forth in the accompanying drawings and the description below. Other features and advantages of the invention will be apparent from the description and drawings, and from the claims.

DESCRIPTION OF DRAWINGS

Like reference symbols in the various drawings indicate like elements.

DETAILED DESCRIPTION

Figure 1A:
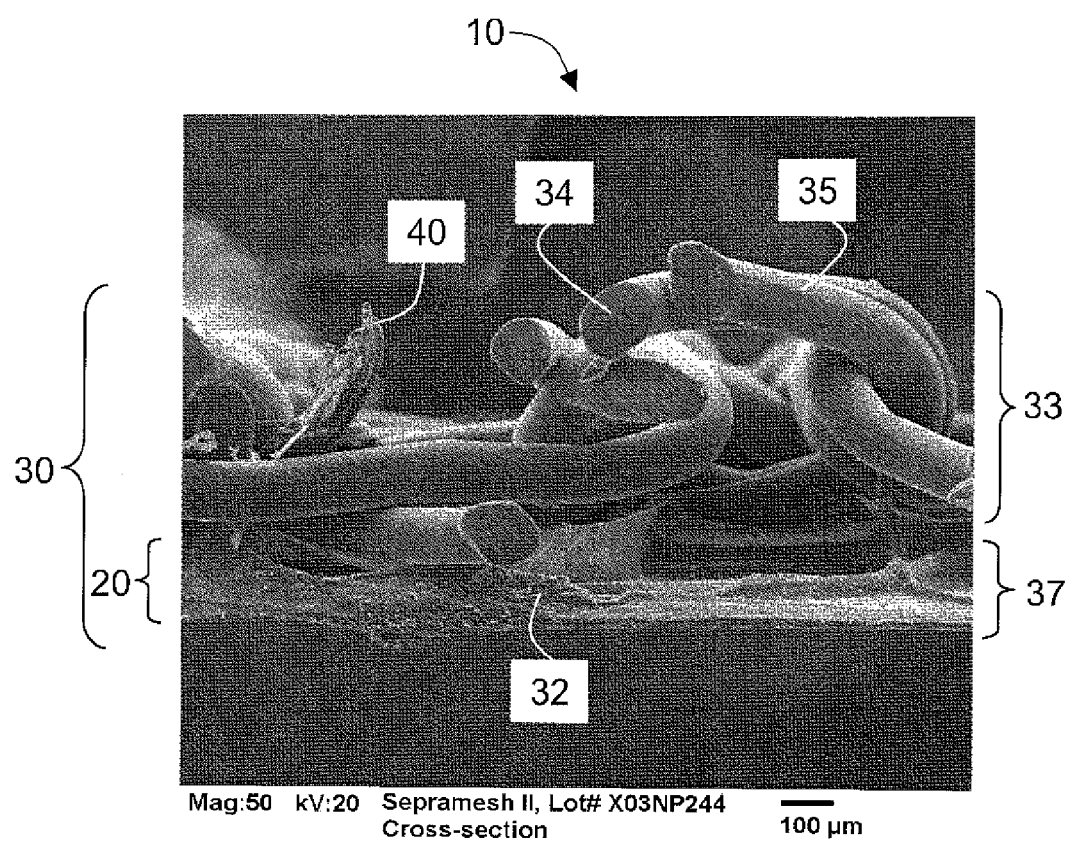
FIG. 1A is a cross-sectional view of an embodiment of a surgical prosthesis.
Figure 1B:
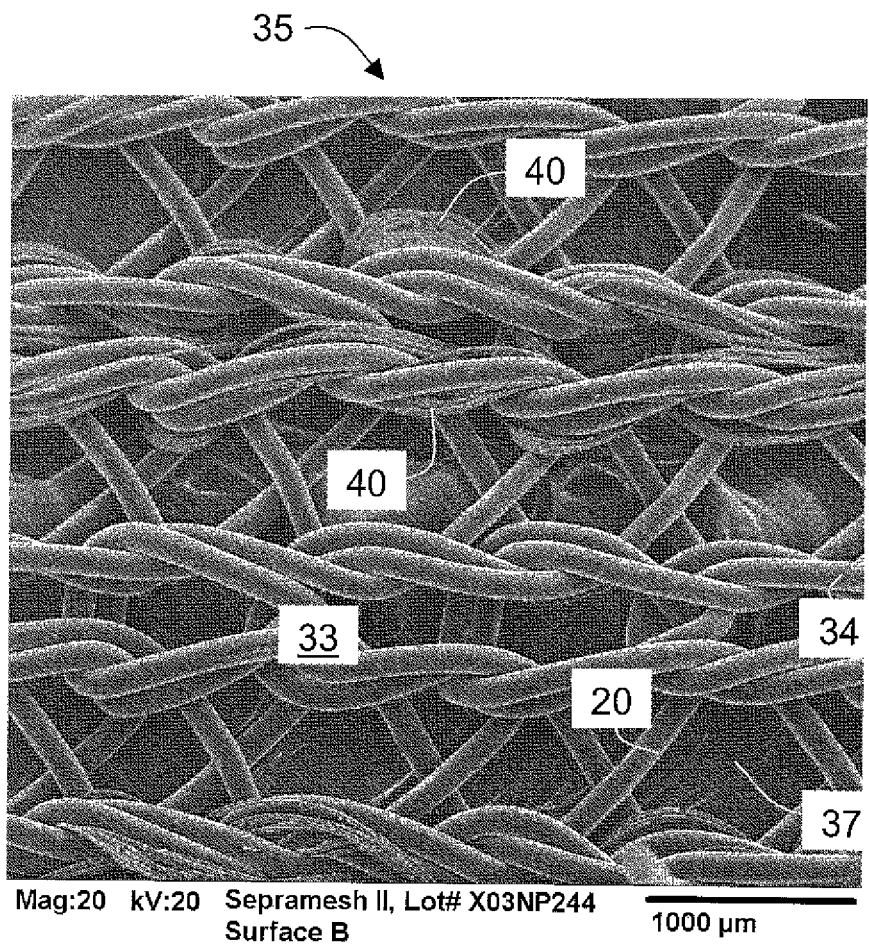
FIG. 1B is a surface view of a first surface of the surgical prosthesis of FIG. 1A.
Figure 1C:
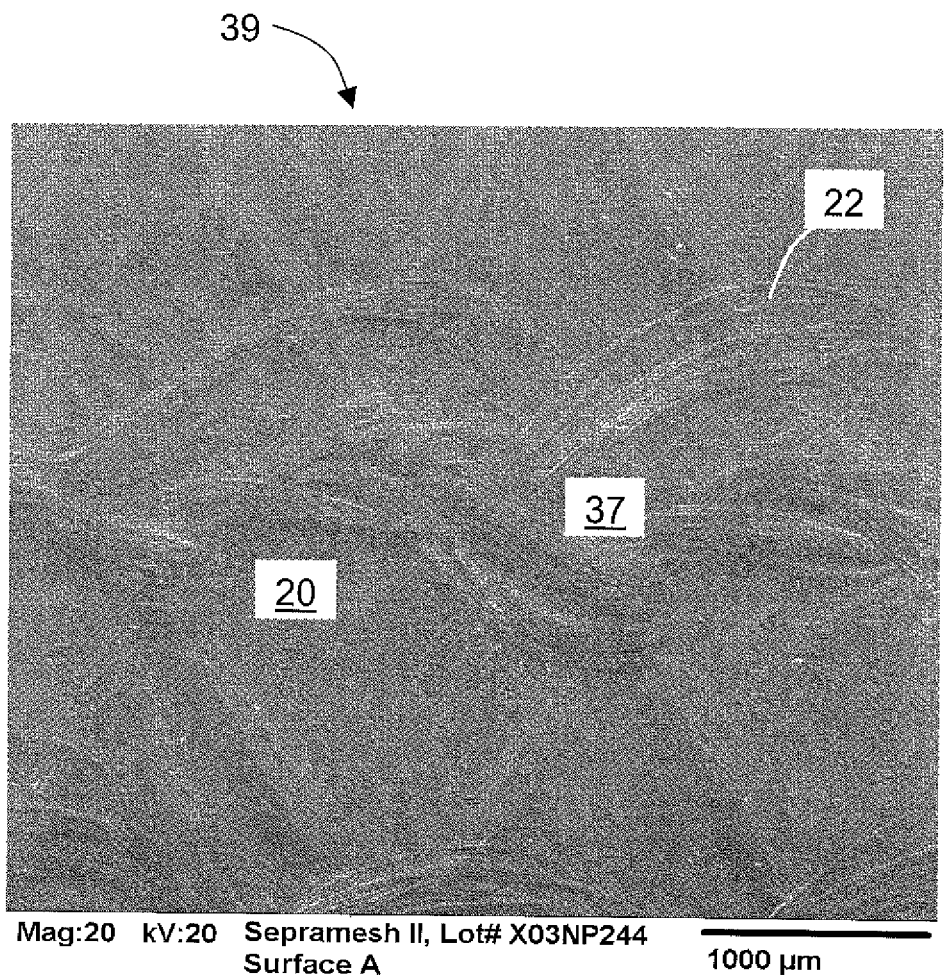
FIG. 1C is a surface view of a second surface of the surgical prosthesis of FIG. 1A.
Figure 2A:
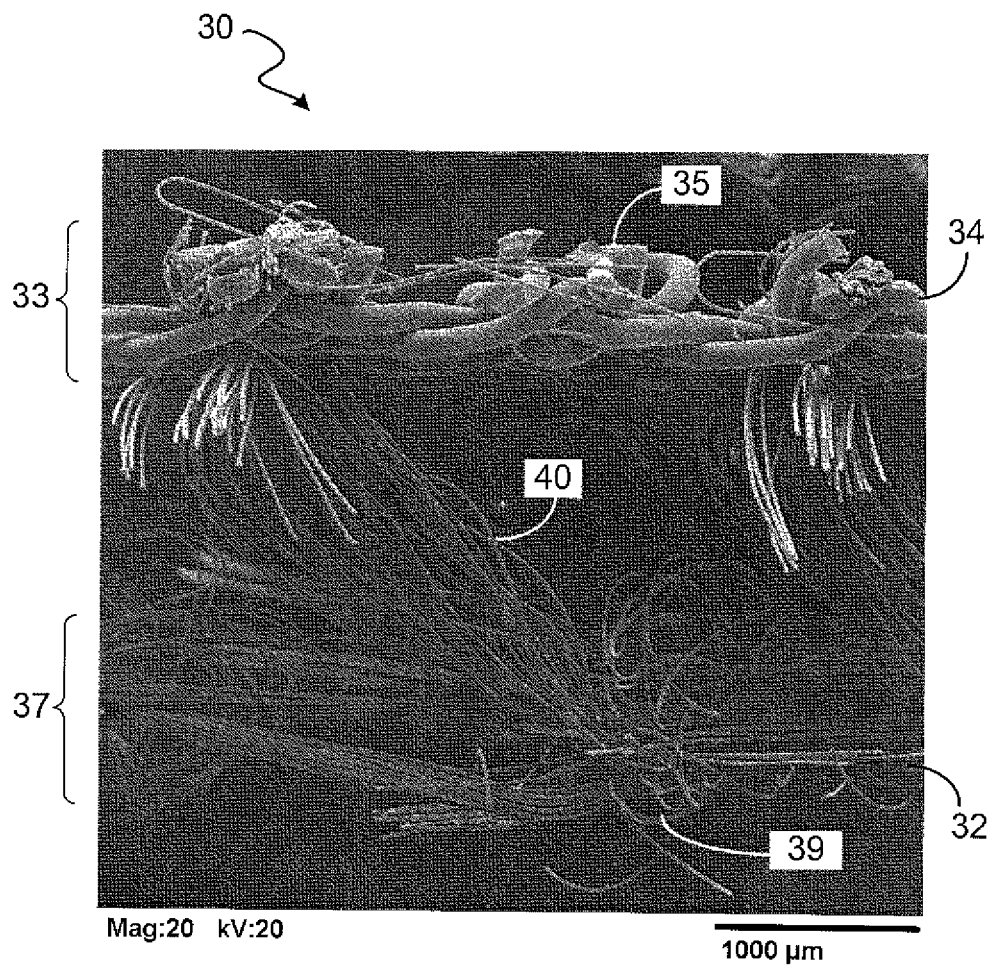
FIG. 2A is a cross-sectional view of a mesh used to form a surgical prosthesis.
Figure 2B:
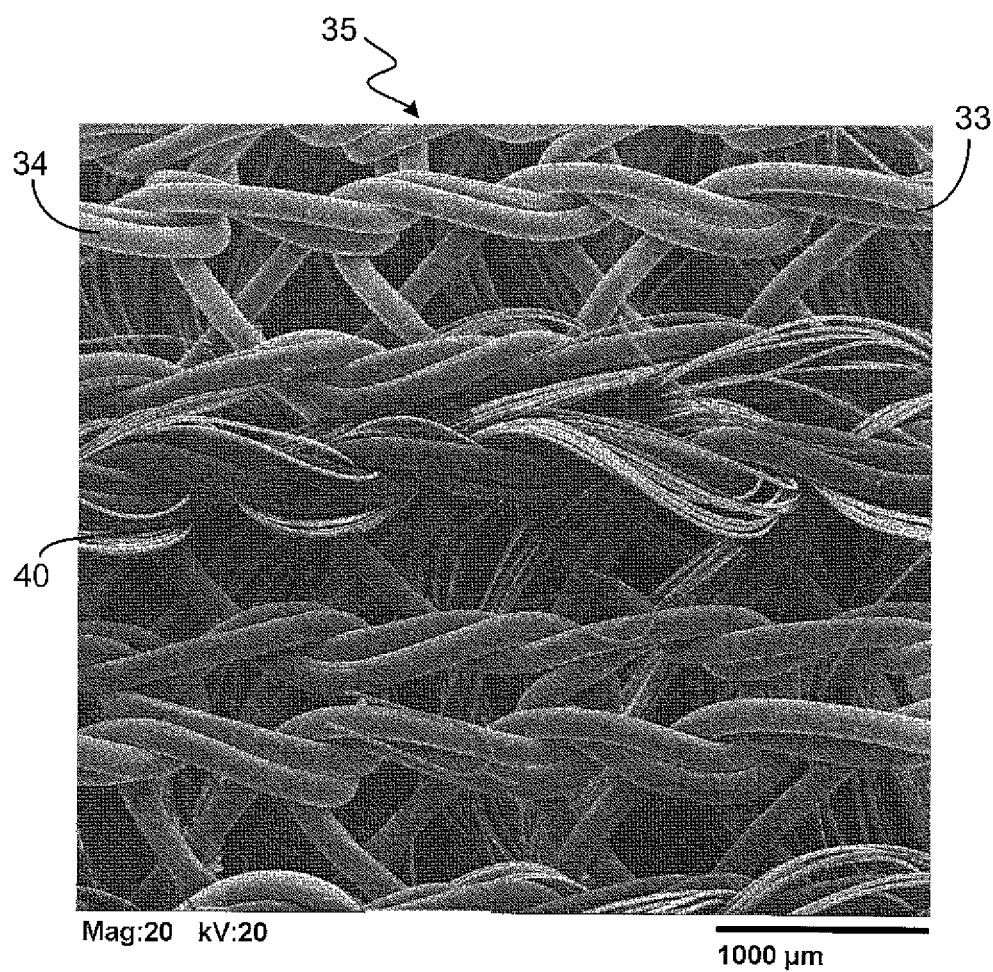
FIG. 2B is a surface view of a non-biodegradable layer of the mesh of FIG. 2A
Figure 2C:
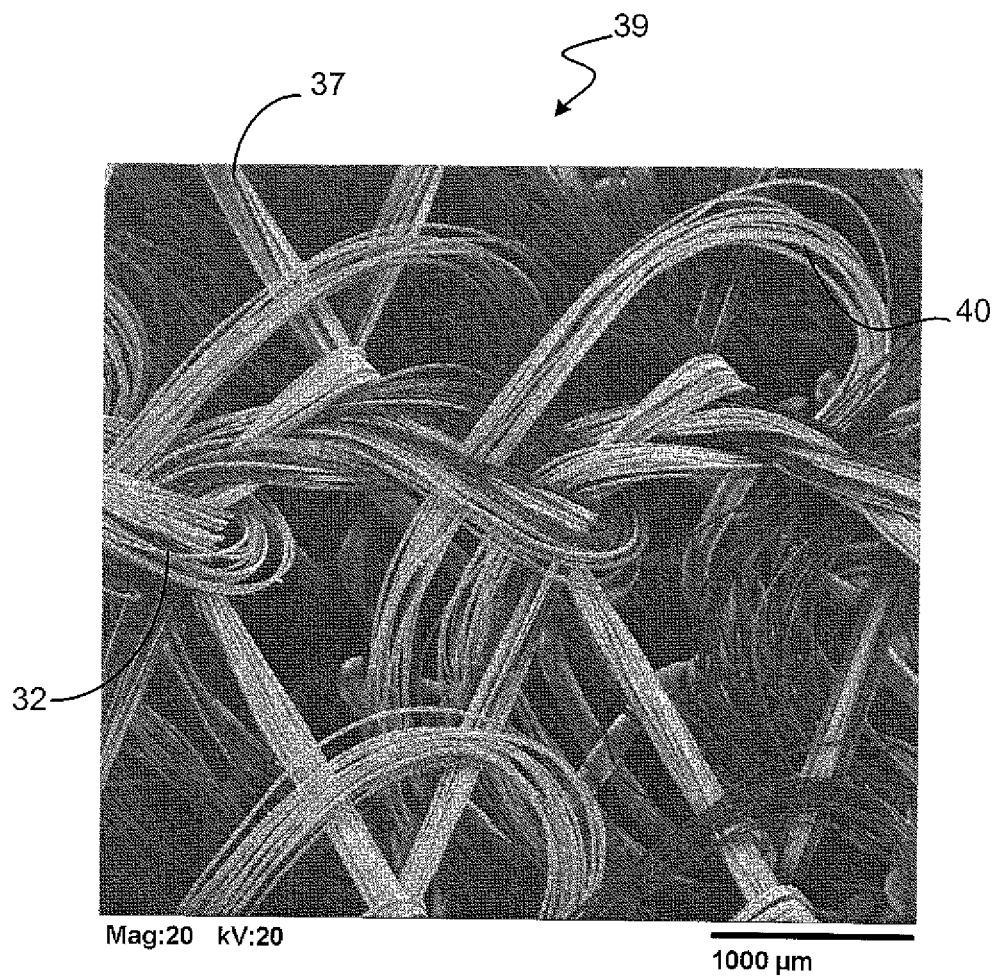
FIG. 2C is a surface view of a biodegradable layer of the mesh of FIG. 2A.

Referring to FIGS. 1A-C, a surgical prosthesis 10 for repairing an unwanted opening in a body cavity, such as an opening in the abdomen, includes an adhesion barrier 20 supported by a three-dimensional mesh 30. The three-dimensional mesh 30, shown with the adhesion barrier 20 in FIGS. 1A-C and without the adhesion barrier 20 in FIGS. 2A-C, is formed of biodegradable yarn 32 and non-biodegradable yarn 34 that define at least two layers (here, two). Referring particularly to FIG. 1B, one of the at least two layers, layer 33, forms a first mesh surface 35 and is substantially non-biodegradable. Referring particularly to FIG. 1C, another of the at least two layers, layer 37, forms a second mesh surface 39 and is substantially biodegradable. Layers 33 and 37 are connected together by a biodegradable binding yarn 40. An adhesion barrier 20, which substantially prevents adhesions from forming on the surgical prosthesis, is formed directly on (e.g., polymerized on) biodegradable layer 37, thereby interconnecting adhesion barrier 20 to mesh 30.

Prior to applying adhesion barrier 20 to mesh 30 to form surgical prosthesis 10, mesh 30 has an uncompressed thickness of between about 2.5 and 3.0 millimeters, an areal density of about 13 to 16 g/ft$^2$, and includes a macroporous structure (e.g., having a pore size of about 100 microns or more) that is accessible from first mesh surface 35 and second mesh surface 39. After applying adhesion barrier 20 to mesh 30 and air drying, surgical prosthesis 10 has a thickness between about 0.45 and 0.9 millimeters, an areal density of about 18 to 21 g/ft$^2$, and includes a macroporous structure that is accessible only from the first mesh surface 35. That is, adhesion barrier 20 is applied to mesh 30 so that adhesion barrier 20 extends past second mesh surface 39 and into the macroporous structure of biodegradable layer 37 of mesh 30, thereby at least partially filling the macroporous structure of layer 37. In some embodiments, the macroporous structure of layer 37 is replaced with a microporous structure (e.g., having a pore size of about 50 microns or less, preferably having a pore size of 10 microns or less).

The Mesh

Figure 3A:
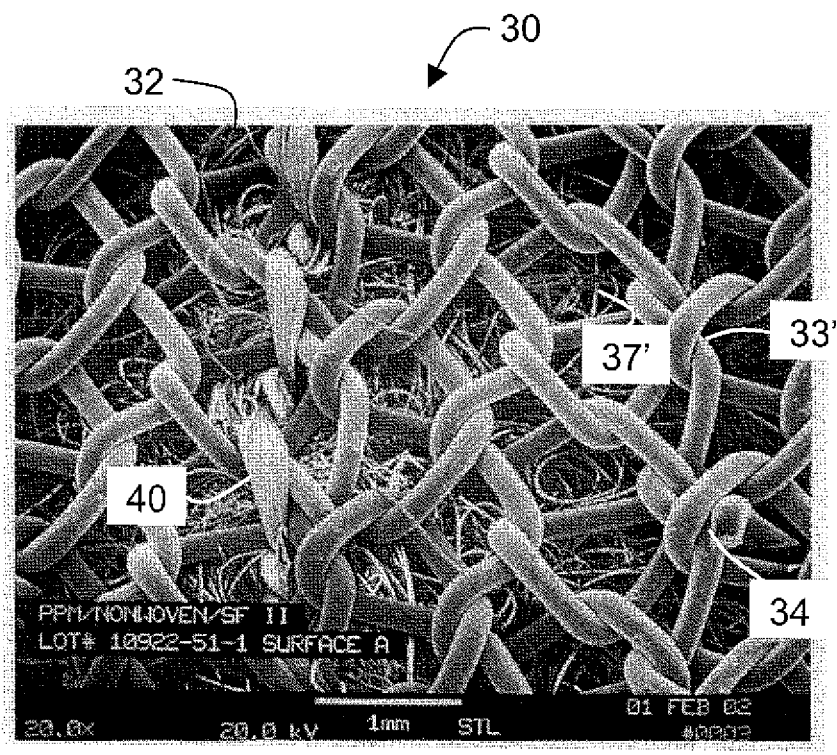
FIG. 3A is a surface view of another embodiment of a mesh used to form a surgical prosthesis.
Figure 3B:
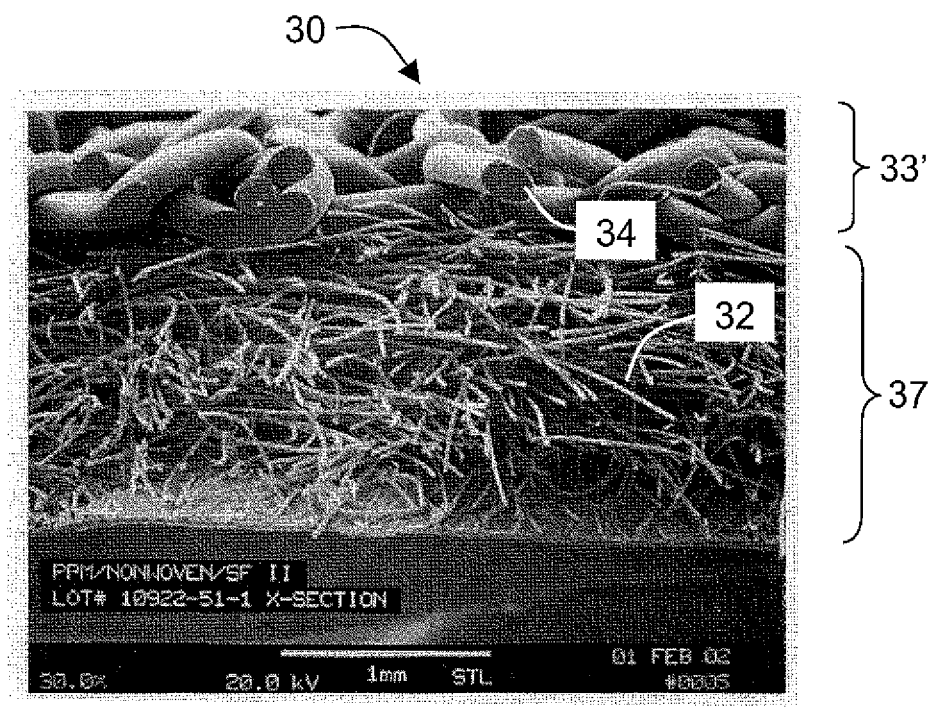
FIG. 3B is a cross-sectional view of the mesh of FIG. 3A.

Mesh 30 is any woven or knitted structure that includes biodegradable yarns 32 and non-biodegradable yarns 34. Typically, the ratio of non-biodegradable yarns to biodegradable yarns in the mesh ranges from about 0.1 to 9. In certain embodiments, the ratio of non-biodegradable yarns to biodegradable yarns is 1 to 2.33. Mesh 30 has a structure that on one side allows adhesion barrier 20 to become entangled and interlocked within biodegradable layer 37, and on the opposite side has a structure that provides a strong support frame for cellular ingrowth and repair. In some embodiments, such as, for example, the embodiment illustrated in FIGS. 2A-C, mesh 30 includes biodegradable and non-biodegradable yarns that have been intertwined and/or interlooped to define layers 33 and 37. In certain embodiment, such as, for example, the embodiment shown in FIGS. 3A-B, mesh 30' includes a preformed non-biodegradable mesh 33' formed of non-biodegradable yarns 34 and a preformed biodegradable mesh 37' formed of biodegradable yarns 32 that are stitched together with biodegradable binding yarn 40.

In general, the non-biodegradable yarn 34 in mesh 30 can be selected as desired. Typically, non-biodegradable yarn 34 is selected to be biocompatible with the subject in whom surgical prosthesis 10 is to be used. In addition, non-biodegradable yarn 34 used in mesh 30 typically has a straight tensile strength between about 1.0 and 2.0 lbs as measured based on a method according to ASTM standard #D2256-95A. In some embodiments, the non-biodegradable yarn 34 is a monofilament yarn having a diameter of about 0.001 inches to about 0.010 inches. In certain embodiments, the non-biodegradable yarn 34 has a diameter of about 0.005 inches. Examples of non-biodegradable yarns include polypropylene and polyethylene terephthalate.

Biodegradable yarns 32, 40 in mesh 30 can also be selected as desired. In general, the biodegradable yarn is selected to be compatible with adhesion barrier 20. In some embodiments, the biodegradable yarn is hydrophilic. In certain embodiments, biodegradable yarns 32 used in mesh 30 has a straight tensile strength between about 0.4 and 1.8 lbs as measured by a method based on ASTM standard #D2256-95A. In some embodiments, the biodegradable yarn is a 90 denier or less multifilament yarn. The multifilament yarn can include 10 to 50 monofilament fibers that each has a thickness of about 0.0006 inches. Examples of biodegradable yarns include poly (glycolic) acid (PGA), polylactic acid (PLA), polydioxanone (PDO), polycaprolactone (PCL), calcium alginate, and copolymers thereof.

In some embodiments, the non-biodegradable and/or biodegradable yarns can be coated with a lubricant in order to facilitate knitting of the yarns. Suitable examples of lubricants for the non-biodegradable and biodegradable yarns include nontoxic hydrophobic waxes such as, for example, esters of fatty acid alcohols, or hydrophilic lubricants such as, for example, polyalkyl glycols. One specific spin finish that yields particularly good results for the non-biodegradable yarn is Lurol PP-3772 (Goulston Technologies, Inc., Monroe, N.C.). A spin finish blend of Poloxamer 184, Polysorbate 20, sodium lauryl sulfate, propylene glycol methyl ether, and toluene has yielded good results for the biodegradable yarn.

The Adhesion Barrier

The adhesion barrier 20 composition may comprise a gel, foam, film or membrane made of a bioresorbable material. The adhesion barrier 20 may be prepared from one or more components selected from hyaluronic acids and any of its salts, carboxymethyl cellulose and any of its salts, oxidized regenerated cellulose, collagen, gelatin, phospholipids, and the first and second polymer systems described below, as well as any crosslinked or derivatized forms thereof. In some embodiments, the barrier is made from a material capable of forming a hydrogel when contacted with an aqueous fluid, such as saline, phosphate buffer, or a bodily fluid.

In a preferred embodiment, the adhesion barrier 20 composition comprises a mixture of at least two polymer systems. The first polymer system includes a crosslinked biodegradable multi-block polymer hydrogel having a three-dimensional polymer network. The second polymer system comprises at least one polyanionic polysaccharide modified by reaction with a carbodiimide compound.

The crosslinked polymer hydrogel of the first polymer system comprises hydrophilic blocks, biodegradable blocks, and crosslinking blocks formed during the polymerization of macromers. The macromers are large molecules that comprise at least one hydrophilic block, at least one biodegradable block and at least one polymerizable group. One or more of these blocks may be polymeric in nature. At least one of the biodegradable blocks comprises a linkage based on a carbonate or ester group, and the macromers can contain other degradable linkages or groups in addition to carbonate or ester groups. Suitable macromers to form polymer hydrogels and methods of preparing them have been described in U.S. Pat. No. 6,083,524 and U.S. Pat. No. 5,410,016, the disclosures of which are incorporated herein by reference.

Suitable hydrophilic polymeric blocks include those which, prior to incorporation into the macromer, are water-soluble such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, hydroxyalkylated celluloses such as hydroxyethyl cellulose and methylhydroxypropyl cellulose, polypeptides, polynucleotides, polysaccharides or carbohydrates such as Ficoll® polysucrose, hyaluronic acid, dextran, heparin sulfate, chondroitin sulfate, heparin, or alginate, and proteins such as gelatin, collagen, albumin, or ovalbumin. The preferred hydrophilic polymeric blocks are derived from poly (ethylene glycol) and poly(ethylene oxide).

The biodegradable blocks are preferably hydrolyzable under in vivo conditions. Biodegradable blocks can include polymers and oligomers of hydroxy acids, carbonates or other biologically degradable polymers that yield materials that are non-toxic or present as normal metabolites in the body. Preferred oligomers or polymers of hydroxy acids are poly(glycolic acid), also called polyglycolate, poly(DL-lactic acid) and poly(L-lactic acid), also called polylactate. Other useful materials include poly(amino acids), poly(anhydrides), poly(orthoesters), and poly(phosphoesters). Polylactones such as poly(epsilon-caprolactone), poly(delta-valerolactone), poly(gamma-butyrolactone) and poly(beta-hydroxybutyrate), for example, are also useful. Preferred carbonates are derived from the cyclic carbonates, which can react with hydroxy-terminated polymers without release of water. Suitable carbonates are derived from ethylene carbonate (1,3-dioxolan-2-one), propylene carbonate (4-methyl-1,3-dioxolan-2-one), trimethylene carbonate (1,3-dioxan-2-one) and tetramethylene carbonate (1,3-dioxepan-2-one).

Polymerizable groups are reactive functional groups that have the capacity to form additional covalent bonds resulting in macromer interlinking. Polymerizable groups specifically include groups capable of polymerizing via free radical polymerization and groups capable of polymerizing via cationic or heterolytic polymerization. Suitable groups include, but are not limited to, ethylenically or acetylenically unsaturated groups, isocyanates, epoxides (oxiranes), sulfhydryls, succinimides, maleimides, amines, imines, amides, carboxylic acids, sulfonic acids and phosphate groups. Ethylenically unsaturated groups include vinyl groups such as vinyl ethers, N-vinyl amides, allyl groups, unsaturated monocarboxylic acids or their esters or amides, unsaturated dicarboxylic acids or their esters or amides, and unsaturated tricarboxylic acids or their esters or amides. Unsaturated monocarboxylic acids include acrylic acid, methacrylic acid and crotonic acid or their esters or amides. Unsaturated dicarboxylic acids include maleic, fumaric, itaconic, mesaconic or citraconic acid or their esters or amides. Unsaturated tricarboxylic acids include aconitic acid or their esters or amides. Polymerizable groups may also be derivatives of such materials, such as acrylamide, N-isopropylacrylamide, hydroxyethylacrylate, hydroxyethylmethacrylate, and analogous vinyl and allyl compounds.

The polymerizable groups are preferably located at one or more ends of the macromer. Alternatively, the polymerizable groups can be located within the macromer. At least a portion of the macromers may contain more than one reactive group per molecule so that the resulting hydrophilic polymer can be crosslinked to form a gel. Macromers having two or more polymerizable groups per molecules are called herein crosslinkers. The minimal proportion of crosslinkers required will vary depending on the desired properties of the hydrogel to be formed and the initial macromer concentration in solution. The proportion of crosslinkers in the macromer solution can be as high as about 100% of all macromers in the solution. For example, the macromers include at least 1.02 polymerizable groups on average, and, more preferably, the macromers each include two or more polymerizable groups on average. Poloxamines, an example of water-soluble polymer component suitable to form a hydrophilic block, have four arms and thus may readily be modified to include four polymerizable groups.

Examples of preferred macromers are illustrated below:
where the polyethylene glycol repeat unit is —($CH_2$—$CH_2$—O)$_x$— or (PEG)$_x$, trimethylene carbonate repeat unit is —(C(O)—O—($CH_2$)$_3$—O)$_w$— or (TMC)$_w$; lactic acid residue is —(O—CH($CH_3$)—CO)$_y$— or (L)$_y$; acrylate residue is $CH_2$=CH—CO— or A, and q, w, w', y, y' and x are integers.

A-(L)$_{y'}$-(TMC)$_{w'}$-[(PEG)$_x$-(TMC)$_{w'}$]$_q$-(L)$_{y'}$-A

A-(L)$_{y'}$-[(PEG)$_x$-(TMC)$_{w'}$]$_q$-(L)$_{y'}$-A

A-[(PEG)$_x$-(TMC)$_{w'}$]$_q$-(L)$_{y'}$-A]

Polymerization of the macromers can be initiated by photochemical means, by non-photochemical like redox (Fenton chemistry) or by thermal initiation (peroxide etc). Suitable photochemical means include exposure of the macromer solution to visible light or UV light in the presence of a photoinitiator such as UV or light sensitive compounds such as dyes, preferably eosin Y.

Polymerization of the macromers may be conducted in the presence of small amounts of monomers which act as accelerant of the polymerization reaction. Preferably the monomers represent 2% or less of the total content of the polymerizable material, more preferably 1% or less, and yet usually about 4,000 ppm. A preferred accelerant is vinyl caprolactam.

In the discussion below and the examples, macromers may be designated by a code of the form xxkZnA$_m$, where xxk represents the molecular weight in Daltons of the backbone polymer, which is polyethylene glycol ("PEG") unless otherwise stated, with x as a numeral and k as the multiplier for thousands; Z designates the molecular unit from which the biodegradable block is derived from and may take the value one or more of L, G, D, C, or T, where L is for lactic acid, G is for glycolic acid, D is for dioxanone, C is for caprolactone, T is for trimethylene carbonate; n is the average number of degradable groups randomly distributed on each end of the backbone polymer; A is for acrylate and m for the number of polymerizable groups per macromer molecules. Thus 20 kTLA$_2$ as used in the Example section is a macromer with a 20×10$^3$ Da polyethylene glycol core with an average of first trimethylene carbonate residues (7 or more residues per macromers, in average about 12) and lactic acid residues (5 or less residues per macromers) sequentially extending on both ends of the glycol core and randomly distributed between both ends then terminated with 2 acrylate groups.

The second polymer system comprises at least one polyanionic polysaccharide modified by a carbodiimide. Methods of preparation of these modified polymers have been described in U.S. Pat. No. 5,017,229 and U.S. Pat. No. 5,527,983, the entire disclosures of which are incorporated herein by reference.

Suitable polyanionic polysaccharides may be selected from one or more of the following, hyaluronic acid, carboxymethyl cellulose, carboxymethyl amylose, carboxymethyl chitosan, chondroitin sulfate, dermatan sulfate, heparin, heparin sulfate, alginic acid, and any of their salts, including sodium, potassium, magnesium, calcium, ammonium or mixtures thereof.

The polyanionic polysaccharides are modified by reaction with a carbodiimide to form N-acyl urea derivatives and render them water insoluble, however, they remain very hydrophilic and thus absorb water to form gels also referred to as hydrogels. The reaction conditions with carbodiimides are well described in the cited patents above. Preferred carbodiimides are those that exhibit water solubility, such as 1-(3-dimethylaminopropyl)-3-ethyl-carbodiimide (EDC) or 1-ethyl-3-(3-dimethylaminopropyl)-carbodiimide methiodide (ETC).

After reaction with carbodiimide, the modified polyanionic polysaccharide compositions may be dried to less than about 20% moisture content, preferably about 9% and stored in powder form.

To prepare the barrier compositions, the modified polyanionic polysaccharide composition may be rehydrated in buffer alone to form a fluid gel before mixing with the macromer solution of the second polymer system. The barrier composition may also be prepared by rehydrating the modified polyanionic polysaccharide composition in the buffer solution of the macromer solution of the second polymer system, thereby forming a fluid gel that comprises both polymer systems. The fluid gel is then cast in a dish having the desired shape and exposed to polymerizing condition, such a UV or visible light to form a barrier composition of the invention. Once the macromers in the fluid gel have polymerized, the barrier composition forms a hydrated soft rubbery material that has improved handling properties and is resistant to tear. The barrier composition may be polymerized into desired shape articles like sheets, discs, tubes or rods by selecting appropriate casts or by extrusion.

The barrier composition may be further dried for packaging and then re-hydrated prior to implantation into the body of a patient (such as a human or animal such as non-human mammals). The barrier composition or shaped article is preferably dried to a moisture content of less than about 5%, and preferably less than about 2% in a convection oven to form a film or membrane, or freeze-dried under a vacuum to form a foam. The barrier composition may be used alone to treat or prevent complications from surgeries (e.g., to prevent the formation of adhesions).

The barrier composition may be deposited on the surface of medical devices such as fabrics (e.g., woven or non-woven fabrics, such as meshes, knits, fleeces and mattes) as a fluid and then dried by any known method. In embodiments in which the barrier composition is in the form of a film or a foam, the barrier composition can be laminated and/or stitched to the fabric by any known method. In embodiments in which the barrier composition is formed from a solution including macromers (e.g., a fluid gel), the barrier composition can be deposited on the fabric by placing the fabric in the fluid gel and initiating polymerization. Hydrophobic fabrics will float on the surface of the fluid gel. Less hydrophobic fabrics, such as fabrics having polar groups (e.g., esters, amides, ketones, and carbonates), may penetrate through the surface into the fluid gel to a certain extent such that polymerization of functional groups on the macromers in the presence of the fabric provides for greater adherence of the barrier composition to the fabric. In composite multilayered fabrics of the invention where one layer is less hydrophobic than the other, when placing the less hydrophobic side of the fabric over the fluid gel, the fibers on that side of the fabric penetrate the fluid gel, while the hydrophobic fibers on the other side of the fabric float over the fluid gel. Once the composition is polymerized, a portion of the polymer network entraps the less hydrophobic fibers of the fabric providing added adhesion strength of the barrier on the fabric.

Once applied to the device or fabric, the barrier composition may be dried for long-term storage and packaging, then rehydrated prior to implantation into the body of a patient.

In general, the adhesion barrier can be in the form of a film, foam, or gel. In some embodiments, the adhesion barrier has a density of less than about 20 grams of total polymer per square foot. In some embodiments, the adhesion barrier has a density of about 4 to about 6 grams of total polymer per square foot. In certain embodiments, the adhesion barrier has a density of about 5 grams of total polymer per square foot.

Figure 4:
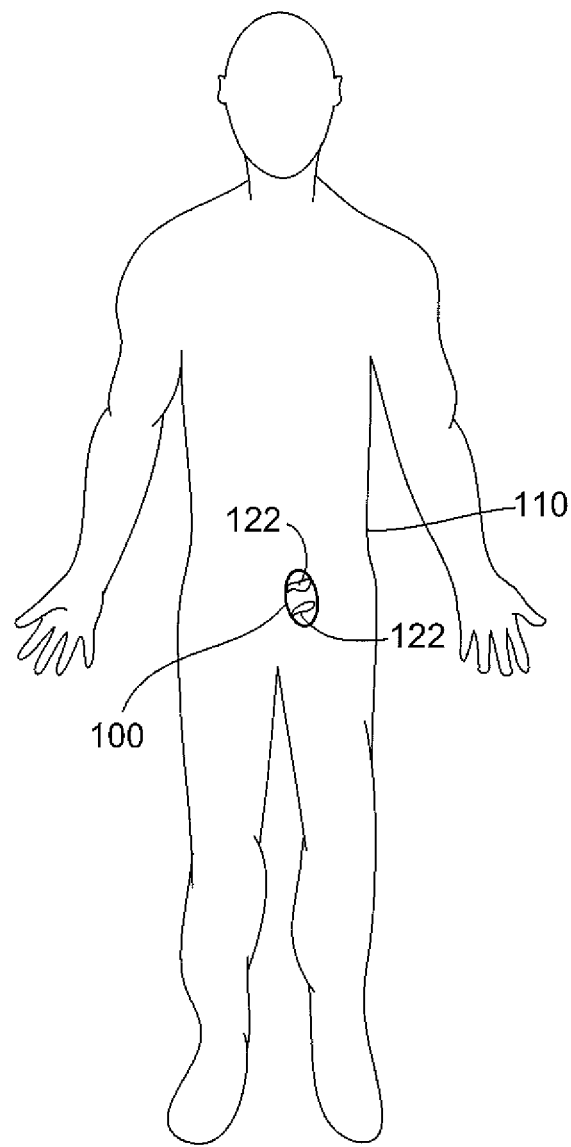
FIG. 4 is a surface view of an opening in a wall of a body cavity before repair.
Figure 5:
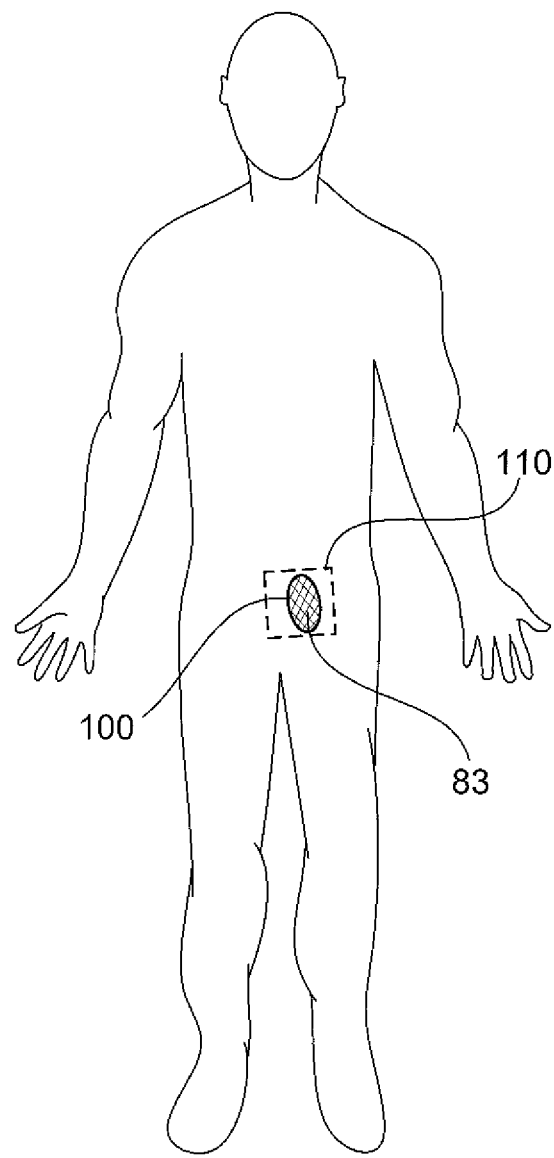
FIG. 5 is a surface view of the opening of FIG. 4 with the surgical prosthesis shown in FIG. 1A properly positioned for repair.
Figure 6:
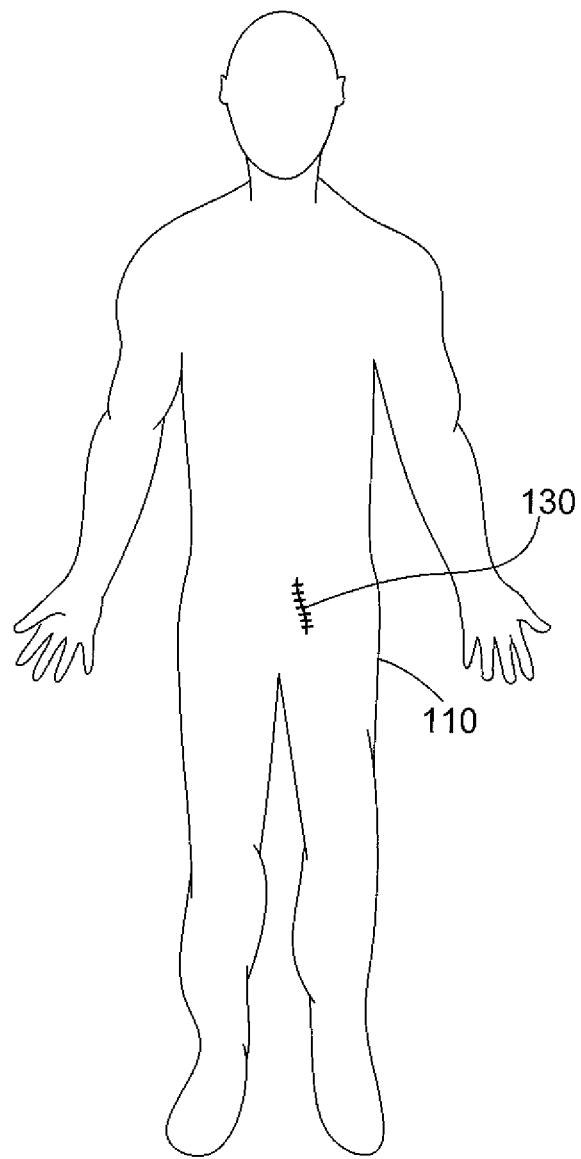
FIG. 6 is a surface view of the opening and surgical prosthesis in FIG. 5, the opening now being closed by sutures.

Referring to FIGS. 4-6, surgical prosthesis 10 can be used to repair an opening 100 in a wall 110 of a patient's body cavity 120 that exposes a visceral surface 122 (e.g., bowels, omentum). To repair opening 100, a medical professional inserts surgical prosthesis 10 through opening 100 and into body cavity 120. Surgical prosthesis 10 is positioned such that layer 37 faces the visceral surface 122 and layer 33 faces wall 110 and covers opening 100. Once the surgical prosthesis 10 is positioned, the medical professional closes opening 100 with sutures 130.

In time, adhesion barrier 20 (e.g., about 3 to 28 days) and layer 37 (e.g., about 60 to 90 days) of mesh 30 are absorbed by the body, leaving layer 33 in contact with visceral surface 122. However, by the time the adhesion barrier 20 has been absorbed, opening 100 has healed to an extent (e.g., a new peritoneal surface has formed over opening 100) that the likelihood of adhesions forming between viscera and surgical prosthesis 10 is minimal. In addition, layer 37, which is formed from biodegradable yarn 32, provides a second defense against adhesion prevention. As described above, layer 37 is absorbed by the body over a period of about 60 to 90 days. As a result, any adhesions that may have formed due to a failure of adhesion barrier 20 or after adhesion barrier 20 was absorbed will be released as layer 37 is absorbed.

While both adhesion barrier 20 and layer 37 are absorbed by a patient's body, layer 33 of the surgical prosthesis 10 becomes incorporated into wall 110. Layer 33, made substantially from non-biodegradable yarn 34, provides a strong, macroporous structure that allows for tissue ingrowth (e.g., layer 33 has a pore size of 100 microns or greater) to repair opening 100.

In general, surgical prosthesis 10 can be prepared using any desired method. In certain embodiments, surgical prosthesis 10 is prepared as follows. First, the three-dimensional mesh 30 is created using biodegradable yarn 32 and non-biodegradable yarn 34. The yarns 32, 34 are threaded into an industrial knitting machine, such as a double-needle bar knitting machine. Yarns 32 and 34 are knitted together using any knitting pattern that creates a three-dimensional macroporous structure having biodegradable layer (e.g., layer 37) and non-biodegradable layer (e.g., layer 33). In certain embodiments, mesh 30 is formed by knitting together a non-biodegradable yarn, a first biodegradable yarn, and a second biodegradable yarn, wherein the non-biodegradable yarn and the first biodegradable yarn form layers 33 and 37 respectively and the second biodegradable yarn binds layers 33 and 37 together. To apply adhesion barrier 20 to mesh 30, a liquid formulation including a photoinitiator and adhesion barrier precursor components is added to a glass tray. Then mesh 30 is placed within the tray with the bioabsorbable side (layer 37) facing the bottom of the tray (e.g., the bioabsorbable layer in fluid contact with the liquid formulation). The liquid formulation is photopolymerized by exposing the tray to a light source that activates the photoinitiator (e.g., a light source having a wavelength of about 450 nm to about 550 nm and an intensity of about 1 mW/cm$^2$ to about 100 mW/cm$^2$). As a result of photoinitiation, a hydrogel is formed within the tray around at least a portion of layer 37. The hydrogel is then dried so that the resulting mesh/hydrogel has a moisture content of less than about 2% (e.g., less than about 1.2%, such as about 0.8%). The mesh/dried hydrogel is then sterilized to form surgical prosthesis 10.

It is believed that the hydrogel does not form within the porous structure of layer 33 during photopolymerization for at least three reasons. First, the amount of liquid formulation added to the glass tray is controlled to produce a hydrogel having a thickness that is equal to or less than the thickness of layer 37. For example, approximately one milliliter of solution including photoinitiator and adhesion barrier precursor components is added per square inch of tray. Then, a mesh having an areal density of 14.5 g/ft$^2$ with a biodegradable layer having an uncompressed thickness of about 2.5 millimeters is added to the tray. Second, because there is an incompatibility between non-biodegradable yarn 34 (e.g., hydrophobic) and the hydrophilic precursor components, the liquid formulation tends not to wick up into the pore structure of layer 33. As result, when the liquid formulation is polymerized it forms the hydrogel only around layer 37. Third, when the polymerized hydrogel, which is mostly water, is air-dried it decreases greatly in thickness. As a result, the adhesion barrier is only around layer 37.

The following examples are illustrative and not intended to be limiting.

Example 1

To manufacture the three-dimensional mesh, two 5 mil polypropylene monofilament fibers (Shakespeare Monofilament and Specialty Polymers, Columbia, S.C.), a 45 denier polyglycolic acid multifilament fiber (Teleflex Medical, Coventry, Conn.), and a 90 denier polyglycolic acid multifilament fiber (Teleflex Medical, Coventry, Conn.) were threaded into a double needle bar knitting machine (Karl Mayer Textimaschinenfabrik GmbH, Oberlshausen, Germany). Referring to FIGS. 2A-C, the fibers were co-knitted by Secant Medical, Perkasie, Pa. using the bar pattern given below to create a mesh that had a layer formed substantially of poly(glycolic) acid on the front (FIG. 2C), a layer formed substantially of polypropylene on the back (FIG. 2B), and a polyglycolic acid binder fiber connecting the two layers together (FIG. 2A).

TABLE 1

Mesh Bar Pattern

| Bar | Fiber | Pattern |
|---|---|---|
| 1 | 5 mil polypropylene monofilament fiber fully threaded | 1/0, 1/2, 2/3, 2/1 |
| 2 | 5 mil polypropylene monofilament fiber fully threaded | 2/3, 2/1, 1/0, 1/2 |
| 3 | 45 denier polyglycolic multifilament fiber half set threaded | 1/0, 1/2 |
| 4 | 90 denier polyglycolic multifilament fiber half set threaded | 1/0, 2/3 |

After fabrication, the three-dimensional mesh was cleaned in a scouring system and annealed at 150° C. in a heat setting frame to stabilize the three-dimensional mesh structure. The resulting three-dimensional mesh had on average 18 wales per inch, 28 courses per inch, a thickness of 0.0319 inches, an areal density of 4.60 ounce per square yard, a burst strength of 762±77 Newtons as measured by a method based on ASTM standard #D3787-89, a tear propagation strength in a direction parallel to the machine direction of 127±21 Newtons and perpendicular to the machine direction of 203±15 Newtons as measured by a method based on ASTM standard #D5587-96, a suture retention strength in the direction parallel to the machine direction of 60±12 Newtons and perpendicular to the machine direction of 80±9 as measured by the pullout force of a 20 gauge needle placed five millimeters from the mesh edge.

Example 2

A liquid formulation including the precursors for adhesion barrier 20 was made as follows. First 1 gram of modified and irradiated hyaluronic acid/carboxymethylcellulose (HA/CMC) powder prepared as described in U.S. Pat. Nos. 5,017, 229 and 5,527,893, was mixed with 86 grams of deionized water under high shear to form a suspension. Next, 2.5 grams of a photopolymerizable compound powder based on poly(ethylene glycol)-trimethlyene carbonate/lactate multi-block polymers endcapped with acrylate esters (20 kTLA$_2$) and described in U.S. Pat. No. 6,177,095, was blended into the suspension. Then, 40 ppm, of Eosin Y, a photoinitiator, 4000 ppm of N-vinylcaprolactam, an accelerant, 0.54 grams of triethanolamine, a buffer and electron transfer component, and 0.8 grams of potassium phosphate, a second buffer, were blended into the suspension. To complete the liquid formulation, additional deionized water was added to bring the final volume to 100 grams.

Example 3

The mesh as described in Example 1 was combined with the adhesion barrier as described in Example 2 to form a surgical prosthesis for soft tissue repair with one surface for tissue ingrowth and one surface with anti-adhesion properties.

To join the adhesion barrier to the mesh, the liquid formulation described in Example 2 was cast onto a glass plate at a casting density of 5 grams of total polymer per square foot. The mesh was placed into the liquid formulation with the polyglycolic acid layer facing the glass plate. The area was illuminated with a visible light from an LED array (450-550 nm) at an intensity of about 4 mW/cm$^2$ for 120 seconds. The photopolymerized composite was dried in a convection oven at 50° C. for 4 hours. The dried composite was peeled from the glass plate, cut to various sizes, packaged, and ethylene oxide sterilized.

Example 4

The surgical prosthesis as prepared in Example 3 was evaluated in a rabbit hernia repair model with abraded bowel.

Twenty sexually mature female New Zealand White Rabbits each weighing between 3 kg and 5 kg at the time of surgery, were anesthetized and subjected to a 5 cm by 7 cm full thickness abdominal muscle excision and cecal abrasion surgical procedure. Each rabbit received either a 5 cm by 7 cm piece of a polypropylene mesh or the surgical prosthesis as prepared in Example 3. All rabbits were allowed to recover from the surgical procedure.

Twenty-eight days after the surgery, the rabbits were euthanized and overall performance of the materials, including adhesion formation and tissue ingrowth was evaluated. Adhesion formation was evaluated and visually scored for extent coverage by adhesion. The following scale was used during the visual examination: 0=no adhesions, 1=25% or less of the defect covered by adhesions, 2=26% to 50% of the defect covered by adhesion, 3=51% to 75% of the defect covered by adhesions, 4=more than 75% of the defect covered by adhesions.

In addition to visual examinations, image analysis was used to calculate the total surface area of the defects and the surface area covered by adhesions. Mechanical testing and SEM samples were also collected and analyzed. The results are described in Tables 2 and 3 below.

TABLE 2

Rabbit Hernia Repair with Abraded Bowel Adhesion Reduction Efficacy Results

| Group N = 10 | Mean Extent of Adhesions | % Defect with Adhesions | % Animals with No Adhesions | % with No Dense Bowel Adhesions |
|---|---|---|---|---|
| Polypropylene Mesh | 2.9 ± 0.3 | 47.3 ± 6.3 | 0 | 0 |
| Surgical Prosthesis as Prepared in Example 3 | 1.3 ± 0.2* | 14.3 ± 5.0* | 0 | 60** |

*p < 0.05 Tukey Kramer HSD analysis
**p < 0.05 Chi-Square analysis

TABLE 3

Rabbit Hernia Repair with Abraded Bowl Tissue Incorporation Results

| Group | Max Load (N) ± SEM |
|---|---|
| Polypropylene Mesh | 33.7 ± 1.2 |
| Surgical Prosthesis as Prepared in Example 3 | 29.7 ± 1.3 |

^p < 0.05 Tukey-Kramer HSD analysis

The results in Table 2 indicate that the surgical prosthesis as described in Example 3 performed significantly well in preventing dense bowel adhesions in vivo. In addition, the surgical prosthesis described in Example 3 had excellent tissue incorporation strength as shown in Table 3.

Example 5

A surgical prosthesis was prepared by placing the bioabsorbable polyglycolic acid side of the mesh as described in Example 1 into 10 to 12 ml of a liquid formulation in a polystyrene dish having an area of 56.7 square centimeters. For the liquid formulation, 2 grams of carbodiimide-modified HA/CMC powder in 90 grams of water was blended with 5% 20 kTLA$_2$ macromer in 100 grams of deionized water. Additional solution consisting of 40 ppm Eosin Y, 4000 ppm N-vinylcaprolactam, 1.08 grams of triethanolamine, and 1.6 grams of potassium phosphate in deionized water were added to bring the final volume to 200 grams.

The liquid formulation was then photopolymerized into a hydrogel using an LED array (450-550 nm) at an intensity of about 4 mW/cm$^2$ for 45 seconds. The mesh with hydrogel was freeze-dried at approximately −30° C. and 200 mTorr, before being peeled from the polystyrene dish. The resulting surgical prosthesis was compressed at 5,000 lbs force for 10 seconds between Teflon coated plates and double packaged in vapor permeable pouches. The surgical prosthesis were sterilized by exposure to ethylene oxide before use.

Using the processes described in Example 4, a 5 cm by 7 cm piece of either a polypropylene mesh or the surgical prosthesis described in this example was implanted in a rabbit hernia repair model with abraded bowel in 10 rabbits for 14 days and in 10 different rabbits for 28 dates. The results are shown in Table 4 below.

TABLE 4

Rabbit Hernia Repair with Abraded Bowel Adhesion Reduction Efficacy Results

| | Mean Extent of Adhesions | % Defect with Adhesions | % Animals with No Adhesions | % with No Dense Bowel Adhesions |
|---|---|---|---|---|
| Group: 14 Days | | | | |
| Polyproylene Mesh | 3.0 ± 0.6 | 65 ± 11 | 0 | 0 |
| Surgical Prosthesis as Prepared in Example 5 | 1.0 ± 0.3* | 16 ± 8* | 20 | 40 |
| Group: 28 Days | | | | |
| Polypropylene Mesh | 2.4 ± 0.3 | 42 ± 13 | 0 | 0 |
| Surgical Prosthesis as Prepared in Example 5 | 1.0 ± 0.1* | 12 ± 3* | 10 | 20 |

*p < 0.05 Tukey Kramer HSD analysis

The adhesion reduction efficacy results showed that the surgical prosthesis described in this example performed well in preventing adhesions in vivo.

Example 6

A liquid formulation of 2.5% 20 kTLA2, 40 ppm of Eosin Y, 4000 ppm of N-vinylcaprolactam, 0.54% of triethanolamine, 0.8% of potassium phosphate, and 1% carbodiimide-modified HA/CMC was prepared and 32 ml of the liquid formulation was cast on a 32 square inch glass plate. The mesh from Example 1 was placed into the liquid formulation with the biodegradable polyglycolic acid side down. The liquid formulation was photopolymerized by exposing the liquid formulation to a visible light emitting diode array having an intensity of about 4 mW/cm$^2$ for four minutes. The resulting mesh reinforced with hydrogel was allowed to air dry at 50° C. for four hours, before the glass plate was removed. The reinforced mesh was then dehydrated at 100° C. for seven hours to form the surgical prosthesis.

Example 7

The surgical prosthesis of Example 6 was tested for surgical handling properties. The abdomino-pelvic cavity of an adult domestic pig was used to simulate a laparoscopic clinical application of the surgical prosthesis.

The surgeon who inserted the surgical prosthesis into the abdomino-pelvic cavity of the adult domestic pig was able to differentiate the correct sidedness of a wet and a dry surgical prosthesis. Before insertion, the surgeon attached stay sutures at each end of the surgical prosthesis. The surgeon then hydrated the surgical prosthesis in saline for a few seconds before delivering the prosthesis through a 12 millimeter trocar. A portion of the stay sutures were passed through the abdominal wall and secured. The surgical prosthesis was tacked to the sidewall using helical titanium tacks. Moderate manipulation of the surgical prosthesis during placement did not cause any delamination. Overall, the surgeon was pleased with the handling, placement, and durability of the surgical prosthesis.

Example 8

A mesh for a surgical prosthesis was formed by stitching together a polyglycolic acid (PGA) nonwoven felt fabric with a mass/area of about 7 mg/cm² and a thickness of about 1 millimeter to a single atlas polypropylene mesh with a mass area of 9.4 mg/cm² and made from 6 mil polypropylene fiber. The PGA nonwoven felt fabric was obtained from Scaffix International (Dover, Mass.) and the single atlas polypropylene mesh was obtained from Genzyme Biosurgery (Fall River, Mass.).

The nonwoven felt fabric was stitched to the polypropylene mesh using Bondek® polyglycolic acid suture size 6-0 (provided by Genzyme Biosurgery, Coventry, Conn. now Teleflex Medical, Coventry, Conn.) in a standard sewing machine. The mass/area of the mesh as stitched together was 16 to 17 mg/cm².

To form a surgical prosthesis, the mesh was placed with the PGA nonwoven felt side down into 10 ml of a 2.5% liquid formulation of 20 kTLA$_2$, 40 ppm of Eosin Y, 4000 ppm of N-vinylcaprolactam, 0.54% of triethanolamine, and 0.8% of potassium phosphate in a polystyrene dish having an area of 56.7 cm². The liquid formulation was photopolymerized into a hydrogel with five 40 second cycles from a xenon light source. The mesh with the hydrogel was freeze-dried at −30° C. and 200 mTorr. A well incorporated, flexible dry sample resulted. The surgical prosthesis was sterilized by exposure to ethylene oxide. After initial hydration, the surgical prosthesis had good wet handling durability.

Example 9

A mesh for a surgical prosthesis was formed using the process described in Example 8. The nonwoven felt fabric side was placed down into a 56.7 cm² polystyrene dish having 12 grams of a suspension including 2.3% carbodiimide-modified HA/CMC as obtained from Genzyme Corporation (Framingham, Mass.) and 0.073 ml of glycerol, a plasticizer. The dish including the suspension and the mesh was left to air-dry overnight.

A high quality composite sample resulted with all components firmly attached and a mass/area ratio of 21.7 mg/cm². Using scanning electron microscopy (SEM), the plasticized HA/CMC membrane was observed to be embedded in the fibers of the nonwoven felt fabric side of the mesh. Some voids, possibly due to air bubbles, were noticeable within the adhesion barrier.

The sample was heated for 7 hours at 100° C. in a convection oven to remove residual moisture. Upon hydration, the hydrophilic, lubricous layer of HA/CMC was visually noticeable on the one surface of the surgical prosthesis. The surgical prosthesis had good wet handling properties after initial hydration and after 24 hours soaking in water at room temperature. The hydrated sample could be rubbed vigorously between thumb and forefingers without delamination and could not be peeled apart by hand.

Example 10

A mesh for a surgical prosthesis was formed using the process described in Example 8. The nonwoven felt fabric side was placed down into a 56.7 cm² polystyrene dish having 5 ml of a 5% solution of 20 kTLA$_2$, 40 ppm of Eosin Y, 4000 ppm of N-vinylcaprolactam, 0.54% of triethanolamine, 0.8% of potassium phosphate, and 5% hyaluronic acid. The solution was then photopolymerized into a hydrogel with four 40 second cycles from a xenon light source obtained from Genzyme Biosurgery (Lexington, Mass.).

The surgical prosthesis had very good wet handling durability and could be used as is or freeze-dried for use at a later time.

Example 11

A mesh for a surgical prosthesis was formed by stitching together a Vicryl® knitted mesh formed of polyglactin 910, a copolymer of poly glycolic and polylactic acid fibers and obtained from Ethicon (New Brunswick, N.J.) to a single atlas polypropylene mesh with a mass area of 9.4 mg/cm² and made from 6 mil polypropylene fiber and obtained from Genzyme Biosurgery (Fall River, Mass.).

The Vicryl® knitted mesh was stitched to the polypropylene mesh using Bondek® polyglycolic acid suture size 6-0 (provided by Genzyme Biosurgery, Coventry, Conn. now Teleflex Medical, Coventry, Conn.) in a standard sewing machine. The mass/area of the mesh as stitched together was about 15 mg/cm².

To form the surgical prosthesis, the mesh was placed with the Vicryl® surface down into 5 ml of a 5% solution of 20 kTLA$_2$, 40 ppm of Eosin Y, 4000 ppm of N-vinylcaprolactam, 0.54% of triethanolamine, and 0.8% of potassium in a polystyrene dish having an area of 56.7 cm³. The solution was then photopolymerized into a hydrogel with four 40 second cycles from a xenon light source. The surgical prosthesis was freeze-dried at −30° C. and 200 mTorr. A well-incorporated, flexible, dry surgical prosthesis resulted. After initial hydration, the surgical prosthesis had good wet handling durability.

All publications, applications, and patents referred to in this application are herein incorporated by reference to the same extent as if each individual publication or patent was specifically and individually indicated to be incorporated by reference in their entirety.

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

Other embodiments are within the scope of the following claims.

What is claimed is:

1. A method of making a surgical prosthesis, the method comprising the steps of:
   providing a fabric comprising a first layer formed substantially of non-biodegradable yarn and a second layer formed of biodegradable yarn;
   providing a liquid formulation comprising macromers and an initiator;
   placing the fabric within the liquid formulation such that the second layer is in fluid contact with the liquid formulation; and
   exposing the liquid formulation to a light source.

2. The method of claim 1, wherein the initiator is a photoinitiator.

3. The method of claim 2, wherein the photoinitiator comprises Eosin Y.

4. The method of claim 1, wherein the liquid formulation further comprises biopolymers, an accelerant and a buffer.

5. The method of claim 4, wherein the biopolymers comprise at least one polyanionic polysaccharide modified by reaction with carbodiimide.

6. The method of claim 4, wherein the buffer comprises triethanolamine.

7. The method of claim 4, wherein the buffer comprises potassium phosphate.

8. The method of claim 4, wherein the accelerant comprises N-vinylcaprolactam.

9. The method of claim 1, wherein the liquid formulation comprises 1 weight percent of carbodiimide-modified hyaluronic acid and carboxymethylcellulose, 2.5 weight percent poly(ethylene glycol)-trimethlyene carbonate/lactate multi-block polymers endcapped with acrylate esters, 40 ppm of Eosin Y, 4000 ppm N-vinylcaprolactam, 0.54 weight percent triethanolamine, 0.8 weight percent of potassium phosphate.

10. The method of claim 1, wherein the light source is an LED array having an intensity of about 1 to about 100 mW/cm2.

11. A method of making a surgical prosthesis, the method comprising the steps of:
providing a fabric comprising a first layer formed substantially of non-biodegradable yarn and a second layer formed of biodegradable yarn;
providing a liquid formulation comprising a first polymer system, a second polymer system, and a photoinitiator;
placing the fabric over the liquid formulation such that the second layer is in fluid contact with the liquid formulation; and
exposing the liquid formulation to a light source to activate the photoinitiator so as to cause polymerization of at least one of the polymer systems in the liquid formulation.

12. The method of claim 11, wherein the polymerization of at least one of the polymer systems results in the formation of a barrier layer partially embedded within the second layer of the fabric.

13. The method of claim 12, wherein the first polymer system comprises carbodiimide-modified hyaluronic acid and carbodiimide-modified carboxymethylcellulose and the second polymer system comprises poly(ethylene glycol)-trimethylene carbonate/lactate multi-block polymers endcapped with acrylate esters.

14. The method of claim 13, wherein the photoinitiator comprises Eosin Y.

15. The method of claim 14, wherein the liquid formulation further comprises an accelerant and at least one buffer.

16. The method of claim 15, wherein the liquid formulation further comprises a first buffer and a second buffer.

17. The method of claim 16, wherein the accelerant comprises N-vinylcaprolactam, the first buffer comprises triethanolamine, and the second buffer comprises potassium phosphate.

18. The method of claim 11, wherein the light source is an LED array having an intensity of about 1 to about 100 mW/cm2.

19. The method of claim 12, further comprising drying the fabric and the barrier layer in a connection oven.

* * * * *